(12) United States Patent
Imaizumi

(10) Patent No.: US 8,876,700 B2
(45) Date of Patent: Nov. 4, 2014

(54) MEDICAL APPARATUS, METHOD FOR CONTROLLING MARKER DISPLAY IN MEDICAL IMAGE AND MEDICAL PROCESSOR

(71) Applicant: Olympus Medical Systems Corp., Tokyo (JP)

(72) Inventor: Katsuichi Imaizumi, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/683,584

(22) Filed: Nov. 21, 2012

(65) Prior Publication Data

US 2013/0158352 A1    Jun. 20, 2013

Related U.S. Application Data

(63) Continuation of application No. PCT/JP2012/057473, filed on Mar. 23, 2012.

(30) Foreign Application Priority Data

May 17, 2011    (JP) ................................ 2011-110728

(51) Int. Cl.
| | |
|---|---|
| *A61B 1/04* | (2006.01) |
| *A61B 1/00* | (2006.01) |
| *A61B 1/06* | (2006.01) |
| *A61B 1/07* | (2006.01) |
| *A61B 1/05* | (2006.01) |
| *A61B 19/00* | (2006.01) |

(52) U.S. Cl.
CPC ........... *A61B 1/0005* (2013.01); *A61B 1/00009* (2013.01); *A61B 1/043* (2013.01); *A61B 1/0638* (2013.01); *A61B 1/00006* (2013.01); *A61B 1/00114* (2013.01); *A61B 1/00117* (2013.01); *A61B 1/00124* (2013.01); *A61B 1/00126* (2013.01); *A61B 1/0019* (2013.01); *A61B 1/00193* (2013.01); *A61B 1/0002* (2013.01); *A61B 1/00039* (2013.01); *A61B 1/00059* (2013.01); *A61B 1/0684* (2013.01); *A61B 1/07* (2013.01); *A61B 1/00188* (2013.01); *A61B 1/051* (2013.01); *A61B 1/0669* (2013.01); *A61B 2019/5289* (2013.01)
USPC ........................... 600/111; 600/103; 600/117

(58) Field of Classification Search
CPC ..... A61B 1/00045; A61B 1/005; A61B 1/043
See application file for complete search history.

(56) References Cited

U.S. PATENT DOCUMENTS 4,895,431 A * 1/1990 Tsujiuchi et al. ............... 359/29
4,999,713 A * 3/1991 Ueno et al. ................. 348/240.3

(Continued)

FOREIGN PATENT DOCUMENTS

| | | |
|---|---|---|
| JP | 05-056918 | 3/1993 |
| JP | 09-322566 | 12/1997 |

(Continued)

OTHER PUBLICATIONS

US 6,692,429, Feb. 17, 2004, Imaizumi et al., (withdrawn).

(Continued)

*Primary Examiner* — Anhtuan T Nguyen
*Assistant Examiner* — Jae Woo
(74) *Attorney, Agent, or Firm* — Scully, Scott, Murphy & Presser, P.C.

(57) ABSTRACT

A processor of an endoscope apparatus that is a medical apparatus generates two images that are a normal-light observation image and a special-light observation image that are obtained by picking up a return light, determines matching of observation fields of view with respect to the two images, generates a marker M that indicates a position on a living tissue for at least one of the two images based on the determination result, causes the generated two images to be displayed within a screen of a monitor, and displays the generated marker M by superimposing the marker M on at least one of the two images.

8 Claims, 6 Drawing Sheets

(56) References Cited

U.S. PATENT DOCUMENTS

| | | | |
|---|---|---|---|
| 5,196,928 A * | 3/1993 | Karasawa et al. | 348/65 |
| 5,583,566 A * | 12/1996 | Kanno et al. | 348/72 |
| 5,662,584 A * | 9/1997 | Hori et al. | 600/103 |
| 5,672,877 A * | 9/1997 | Liebig et al. | 250/363.04 |
| 6,293,911 B1 * | 9/2001 | Imaizumi et al. | 600/160 |
| 6,322,497 B1 * | 11/2001 | Takahashi | 600/118 |
| 7,110,586 B2 * | 9/2006 | Bacus et al. | 382/128 |
| 7,179,222 B2 * | 2/2007 | Imaizumi et al. | 600/109 |
| 7,520,854 B2 * | 4/2009 | Sato | 600/118 |
| 8,004,560 B2 * | 8/2011 | Sato et al. | 348/65 |
| 8,270,691 B2 * | 9/2012 | Xu et al. | 382/128 |
| 2006/0173358 A1 | 8/2006 | Xie | |
| 2007/0013771 A1 * | 1/2007 | Imaizumi et al. | 348/74 |
| 2007/0142705 A1 * | 6/2007 | Ohnishi et al. | 600/109 |
| 2008/0091065 A1 * | 4/2008 | Oshima et al. | 600/109 |
| 2008/0207997 A1 * | 8/2008 | Higgins et al. | 600/114 |
| 2009/0213140 A1 * | 8/2009 | Ito et al. | 345/629 |
| 2010/0128116 A1 * | 5/2010 | Sato et al. | 348/65 |
| 2010/0317920 A1 * | 12/2010 | Doi et al. | 600/109 |
| 2012/0130171 A1 * | 5/2012 | Barak et al. | 600/117 |

FOREIGN PATENT DOCUMENTS

| | | |
|---|---|---|
| JP | 2006-230906 | 9/2006 |
| JP | 2007-020728 | 2/2007 |
| JP | 2010-075368 | 4/2010 |
| JP | 2010-172673 | 8/2010 |
| JP | 2010172673 A * | 8/2010 |

OTHER PUBLICATIONS

Extended Supplementary European Search Report dated Feb. 4, 2014 from related European Application No. 12 78 6034.4.

* cited by examiner

MEDICAL APPARATUS, METHOD FOR CONTROLLING MARKER DISPLAY IN MEDICAL IMAGE AND MEDICAL PROCESSOR

CROSS REFERENCE TO RELATED APPLICATION

This application is a continuation application of PCT/JP2012/057473 filed on Mar. 23, 2012 and claims benefit of Japanese Application No. 2011-110728 filed in Japan on May 17, 2011, the entire contents of which are incorporated herein by this reference.

BACKGROUND OF THE INVENTION

1. Field of the Invention

The present invention relates to a medical apparatus, a method for controlling marker display in a medical image and a medical processor, and more particularly to a medical apparatus, a method for controlling marker display in a medical image and a medical processor that can display a marker on an image.

2. Description of the Related Art

Conventionally, medical apparatuses capable of displaying medical images have been widely used. For example, an endoscope apparatus is a medical apparatus that can display, on a monitor, an image of a living tissue that is obtained by being picked up by an image pickup device that is provided at a distal end of an insertion portion by the elongated insertion portion having flexibility being inserted into a body cavity of a subject. A surgeon can perform diagnosis, treatment and the like of an observed site while the surgeon is watching the medical image.

Some medical apparatuses can display two images on one monitor when the medical apparatuses display medical images on the monitors. For example, some endoscope apparatuses can acquire normal-light observation images and special-light observation images with respect to the same sites to be examined. Accordingly, a surgeon displays a normal-light observation image and a special-light observation image side by side on a monitor simultaneously, and can perform diagnosis, treatment and the like.

Further, as disclosed in, for example, Japanese Patent Application Laid-Open Publication No. 2010-172673, the endoscope apparatus having the function of displaying a marker on a displayed image is also proposed, or put to practical use. A surgeon can clearly point out an optional position on the screen by the marker.

SUMMARY OF THE INVENTION

A medical apparatus of one aspect of the present invention includes an imager that picks up an image of a light from a living tissue, an image processor that generates a first image picked up in a first observation field of view in the imager, and a second image picked up in a second observation field of view in the imager, a discriminator that determines matching of the first observation field of view and the second observation field of view, and processor that performs processing for displaying markers indicating same positions for the first image and the second image when it is determined that the first observation field of view and the second observation field of view match each other in the discriminator, and a display that simultaneously displays the first image and the second image processed in the processor.

A method for controlling marker display in a medical image of one aspect of the present invention includes picking up an image of a light from a living tissue, generating a first image picked up in a first observation field of view, and a second image picked up in a second observation field of view, determining matching of the first observation field of view and the second observation field of view, performing processing for displaying markers indicating same positions for the first image and the second image when it is determined that the first observation field of view and the second observation field of view match each other, and simultaneously displaying the first image and the second image for which the processing is performed.

A medical processor of one aspect of the present invention is a medical processor that processes an image picked up by an imager that picks up an image of a light from a living tissue, and includes an image processor that generates a first image picked up in a first observation field of view in the imager, and a second image obtained by being picked up in a second observation field of view in the imager, a discriminator that determines matching of the first observation field of view and the second observation field of view, a processor that performs processing for displaying markers indicating same positions for the first image and the second image when it is determined that the first observation field of view and the second observation field of view match each other in the discriminator, and an output section that outputs a signal for simultaneously displaying the first image and the second image processed in the processor.

DETAILED DESCRIPTION OF THE PREFERRED EMBODIMENT

Hereinafter, an embodiment of the present invention will be described with reference to the drawings.

(Configuration)

Figure 1:
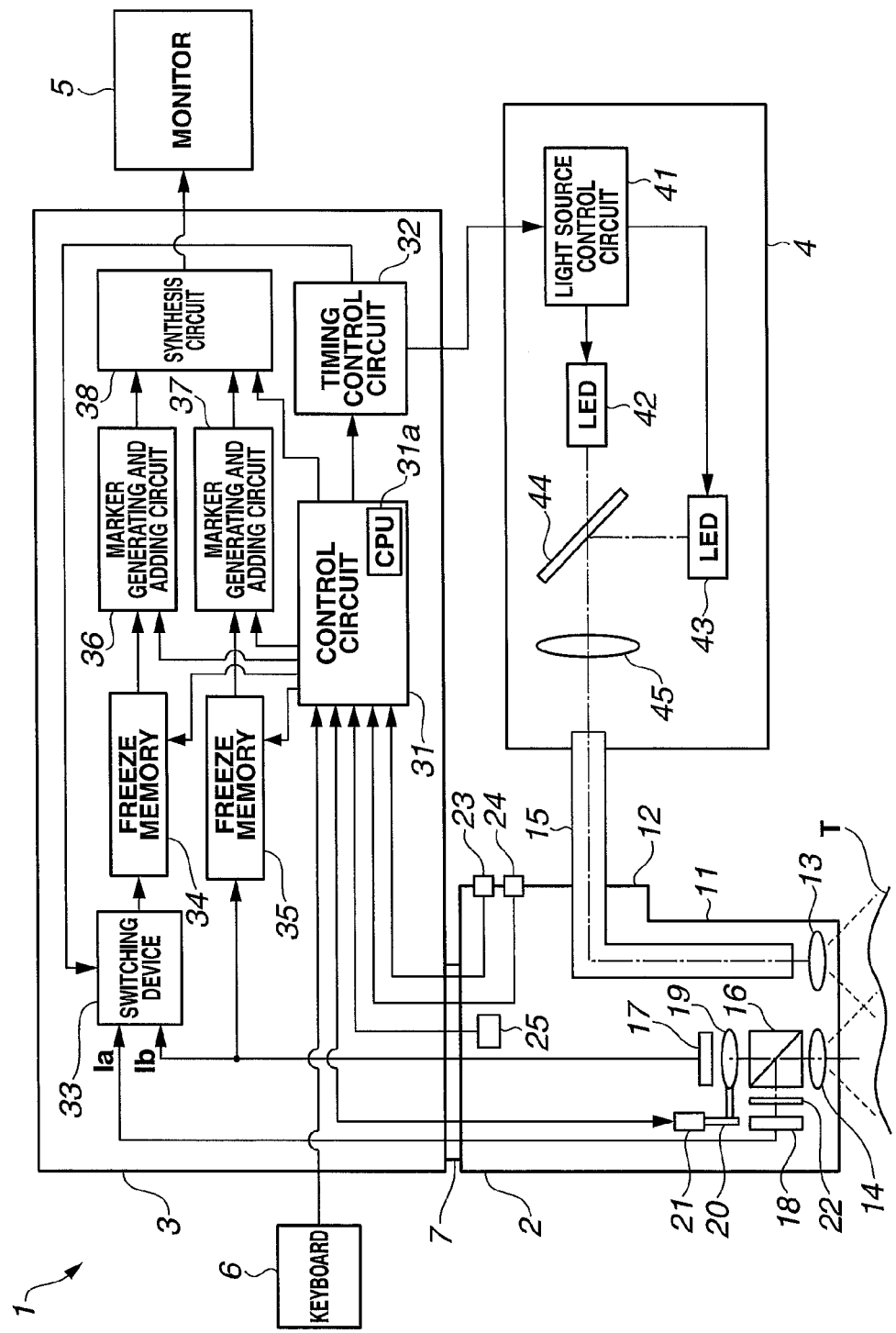
FIG. 1 is a schematic configuration diagram showing a configuration of an endoscope apparatus according to an embodiment of the present invention.

FIG. 1 is a schematic configuration diagram showing a configuration of an endoscope apparatus according to the present embodiment. An endoscope apparatus 1 which is a medical apparatus includes an endoscope 2, a processor 3 and a light source apparatus 4, and a monitor 5 which is a display apparatus and a keyboard 6 which is an input apparatus are connected to the processor 3 which is a medical processor. The endoscope 2 is connected to the processor 3 by a universal cable 7. Further, the light source apparatus 4 is connected to the endoscope 2 so as to supply an illuminating light, and is connected to the processor 3 so as to receive a control signal. The endoscope 2 is detachably connected to the processor 3 by a connector (not illustrated) of the universal cable 7.

The endoscope 2 includes an elongated insertion portion 11 and an operator 12. At a distal end portion of the insertion portion 11, an illuminating lens 13 and a lens 14 as an objective optical system are provided. A light guide 15 is inserted through the insertion portion 11, and behind the illuminating lens 13, an end face of a distal end side of the light guide 15 is disposed. A proximal end side of the light guide 15 is connected to the light source apparatus 4 so that the light guide 15 transmits the illuminating light from the light source apparatus 4. At the proximal end portion of the light guide 15, a connector not illustrated is provided, and the light guide 15 of the endoscope 2 is detachably connected to the light source apparatus 4.

At a rear of the lens 14 as an objective optical system, a half mirror 16 is provided. The half mirror 16 functions so as to direct a return light from a living tissue T of a subject to two image pickup devices 17 and 18.

An imager is provided at the distal end portion of the insertion portion 11. The CCD 17 which is one of the image pickup devices of the imager is an image pickup device for normal-light observation, and is disposed so as to receive the light from the half mirror 16 through a lens 19 that functions as a zoom lens. The lens 19 is connected to an actuator 21 via a support member 20 that supports the lens 19. The CCD 17 is an image pickup device for normal-light observation. That is to say, the imager has the lens 19 which is a zoom lens that makes an observation field of view range variable.

The actuator 21 is an actuator that has a multilayer piezoelectric element with a plurality of piezoelectric layers being stacked in layer and a detector that is provided at a part of the multilayer piezoelectric element and detects distortion or stress which is generated by the multilayer piezoelectric element, as disclosed in, for example, Japanese Patent Application Laid-Open Publication No. 09-322566. The actuator 21 is driven by a drive signal from a control circuit (described later) of the processor 3. The actuator 21 moves the support member 20 along an optical axis of the lens 19, and thereby, a zoom function by the lens 19 is achieved.

Further, the actuator 21 outputs a termination position signal that indicates that the actuator reaches a termination of a drive stroke from the detected distortion or stress. The termination position signal which the actuator 21 outputs is supplied to the processor 3. When the termination position signal is outputted from the actuator 21, it indicates that the lens 19 is at a position at a time of the widest angle. The termination position signal from the actuator 21 is retained in the processor 3 when a freeze button 23 which will be described later is pressed down.

Note that in FIG. 1, it is detected based on the termination position signal of the actuator 21 that the lens 19 is at the position at the time of the widest angle, but it may be detected by, for example, a limit switch which the support member 20 contacts that the lens 19 is located at the position at the time of the widest angle.

Further, a CCD 18 which is the other image pickup device of the imager is an image pickup device for fluorescence observation which is one kind of special-light observation, and is disposed to receive the light from the half mirror 16 via an excitation light cut filter 22. The CCD 18 is an image pickup device for special-light observation.

Accordingly, the endoscope 2 has an imager including the CCD 17 which is an imager that picks up an image of a return light that is a reflected light of a light for normal-light observation, and the CCD 18 which is an imager that picks up an image of a return light of a light for special-light observation.

The light received by the CCD 17 is a return light from the living tissue T, and the return light is a reflected light of a white color light for normal-light observation. The light received by the CCD 18 is a return light from the living tissue T, and the return light is fluorescence that is emitted by a substance excited by an excitation light for fluorescence observation. In other words, the CCDs 17 and 18 configure the imager, that is, an image pickup apparatus which picks up an image of the return light of the light with which the living tissue T is irradiated by the illuminating light from the light source apparatus 4.

In FIG. 1, the endoscope 2 is not provided with a zoom function for fluorescence observation. An angle of view of an image obtained in the CCD 18 is the same as an angle of view of the image which is obtained at the time of the widest angle in the CCD 17. The lens 14 which is a common objective optical system is used, and therefore, when the angle of view of the image obtained in the CCD 18, and the angle of view of the image which is obtained at the time of the widest angle in the CCD 17 are the same, the observation fields of view with respect to the two images match each other.

The termination position signal that is outputted from the actuator 21 is inputted in a control circuit 31. Subsequently, as will be described later, the control circuit 31 determines matching of the observation fields of view with respect to the two images obtained by the CCDs 17 and 18 based on the termination position signal. The termination position signal can be said as zoom information of the lens 19 which is a zoom lens. Accordingly, the control circuit 31 configures an observation field of view discriminator that determines matching of the observation fields of view with respect to the two images. Subsequently, the control circuit 31 which is the observation field of view discriminator determines matching of the observation fields of view based on the zoom information of the zoom lens.

The operator 12 is provided with various switches for a surgeon to operate. In FIG. 1, the freeze button 23 and a release button 24 are shown. The freeze button 23 is a button for obtaining a still image. The release button 24 is a button for storing the still image, which is obtained by being frozen, in a storage apparatus not illustrated.

Further, an identification information storage 25 which stores identification information showing the kind of the endoscope 2 is provided in the operator 12.

The processor 3 includes the control circuit 31, a timing control circuit 32, a switching device 33, freeze memories 34 and 35, marker generating and adding circuits 36 and 37 and a synthesis circuit 38.

The control circuit 31 includes a central processing unit (hereinafter, called a CPU) 31a, receives an operation signal from the keyboard 6, and performs control of the entire processor 3 to execute various kinds of processing based on the received operation signal. The control circuit 31 is a controller which executes various kinds of processing designated by a user by executing a predetermined software program stored in a ROM (not illustrated) in response to various commands inputted in the keyboard 6.

Furthermore, the control circuit 31 also receives various signals from the endoscope 2. More specifically, the control circuit 31 receives the termination position signal from the actuator 21, respective operation signals from the freeze button 23 and the release button 24, and the identification information from the identification information storage 25.

Note that FIG. 1 shows only the circuits relating to simultaneous display of two still images, and circuits for the other functions, for example, a drive circuit and a signal line of the drive signal which is supplied from the processor 3 for driving the CCDs 17 and 18, are omitted.

Furthermore, the control circuit 31 supplies control signals to the timing control circuit 32, the freeze memories 34 and 35, and the marker generating and adding circuits 36 and 37. When the control circuit 31 receives a freeze instruction by pressing down of the freeze button 23, the control circuit 31 outputs a predetermined signal to the freeze memories 34 and 35. When the control circuit 31 receives a display instruction of a marker from the keyboard 6, the control circuit outputs a predetermined signal to the marker generating and adding circuits 36 and 37. Further, the control circuit 31 reads the identification information of the identification information storage 25 of the endoscope 2, and supplies the control signal corresponding to the read identification information to the timing control circuit 32, and causes the timing control circuit 32 to output various timing signals corresponding to the kind of the endoscope 2.

The timing control circuit 32 supplies timing signals corresponding to various modes and the kind of the endoscope 2 to various circuits. In FIG. 1, the timing control circuit 32 supplies timing signals to the light source apparatus 4 and the switching device 33.

The switching device 33 is a circuit that can receive two video signals Ia and Ib, and selects and outputs one of the two video signals Ia and Ib based on the timing signal from the timing control circuit 32. That is to say, the switching device 33 performs selection of the two video signals Ia and Ib in accordance with the kind of the endoscope connected to the processor 3.

In FIG. 1, the endoscope 2 is connected, and therefore, the video signals Ia and Ib from the two CCDs 17 and 18 are inputted in the switching device 33, but the switching device 33 is controlled to select the video signal Ia at all times and output the video signal Ia to the freeze memory 34, based on the timing signal from the timing control circuit 32. In other words, when the endoscope 2 is connected, the timing control circuit 32 supplies such a timing signal as to select and output the video signal Ia at all times to the switching device 33.

The freeze memory 34 is a memory for a still image, which stores the video signal outputted from the switching device 33, based on the control signal from the control circuit 31, and the freeze memory 35 is also a memory for a still image, which stores the video signal from the CCD 17, based on the control signal from the control circuit 31.

The timing control circuit 32, the switching device 33 and the freeze memories 34 and 35 configure an image processor that generates two images that are the normal-light observation image and the special-light observation image which are obtained by picking up images of the return light synchronously with irradiation of the light for normal-light observation and the light for special-light observation.

The marker generating and adding circuits 36 and 37 are circuits that respectively perform processing of generating image signals of markers to be superimposed on the video signals from the freeze memories 34 and 35 and adding the image signals of the markers to the video signals, and outputs the respective video signals to which the markers are added to the synthesis circuit 38. The marker generating and adding circuits 36 and 37 add markers to the inputted video signals based on the control signal from the control circuit 31. That is to say, the marker generating and adding circuits 36 and 37 respectively execute the processing of adding markers to the inputted video signals or adding no markers to the inputted video signals, based on the control signal from the control circuit 31. As a result, the marker generating and adding circuits 36 and 37 output the images to which markers are added or not added. As will be described later, the control circuit 31 and the marker generating and adding circuits 36 and 37 configure a marker generator that generates a marker indicating a position on a living tissue to at least one of two images based on the determination result of the observation field of view discriminator.

Though not illustrated, when the control circuit 31 receives a release instruction by pressing down of the release button 24, the control circuit 31 executes the processing of storing the output signals of the freeze memories 34 and 35 or the marker generating and adding circuits 36 and 37 into a storing apparatus not illustrated.

The synthesis circuit 38 is a circuit for synthesizing the two images outputted from the marker generating and adding circuits 36 and 37 to display the two images side by side on the screen of the monitor 5 simultaneously. Accordingly, on the screen of the monitor 5 which receives the video signal from the synthesis circuit 38, the two images of the normal-light observation image and the special-light observation image are simultaneously displayed side by side. When the user inputs a command that instructs simultaneous display of the two images to the keyboard 6, the control circuit 31 outputs the control signal to display the two images simultaneously to the synthesis circuit 38.

Accordingly, the synthesis circuit 38 configures a display that displays the two images generated by the image processor within a screen 5a which is one screen of the monitor 5, and displays the marker generated by the marker generator by superimposing the marker on at least one of the two images.

When the user does not input the command to instruct simultaneous display of the two images to the keyboard 6, the control circuit 31 outputs a control signal to display one of the two images to the synthesis circuit 38.

The light source apparatus 4 includes a light source control circuit 41, two LEDs 42 and 43 which are light-emitting elements, a half mirror 44, and a condenser lens 45.

The light source control circuit 41 generates a drive signal to the LEDs 42 and 43 and outputs the drive signal based on the timing signal from the timing control circuit 32.

The LED 42 is a light-emitting element that emits a white color light for normal-light observation, and the LED 43 is a light-emitting element that emits an excitation light of a predetermined wavelength band for fluorescence observation. When the endoscope apparatus 1 is in an operation mode which outputs both of a normal-light observation image and a fluorescence observation image, the light source control circuit 41 alternately supplies a predetermined drive signal to the LEDs 42 and 43, and thereby the LEDs 42 and 43 are exclusively driven alternately. Accordingly, the light source apparatus 4 configures an illuminator or an illumination apparatus which can irradiate the living tissue T with the light for normal-light observation and the light for special-light observation.

The illuminating lights from the LEDs 42 and 43 are directed to the condenser lens 45 through the half mirror 44, and the condenser lens 45 condenses the illuminating lights on an end face of the proximal end side of the light guide 15 which is connected to the light source apparatus 4. Accordingly, the illuminating light is emitted from the end face of the distal end side of the light guide 15 through the light guide 15. The illuminating light emitted from the end face of the distal end side of the light guide 15 is emitted from the distal end portion of the insertion portion 11 via the illuminating lens 13 and illuminates the living tissue T of the site to be observed.

Figure 2:
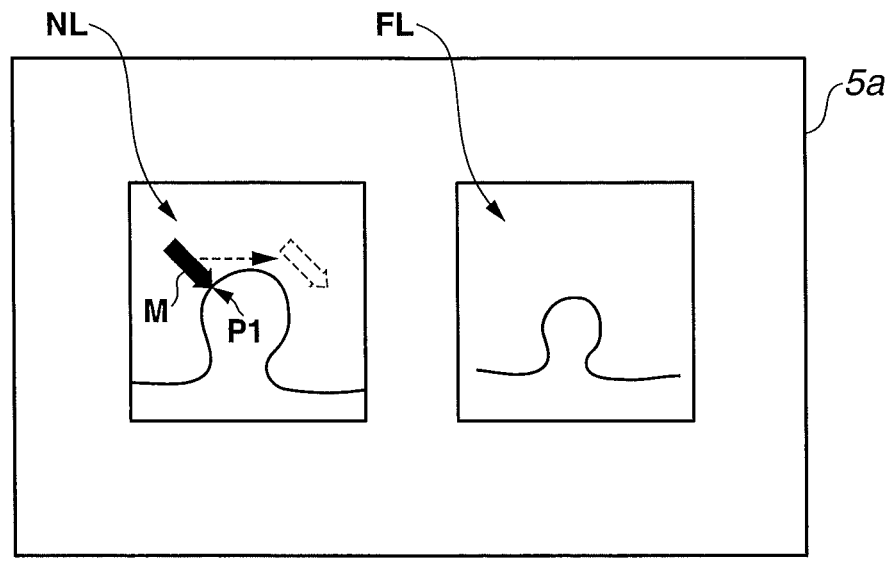
FIG. 2 is a view showing a display example of two images, according to the embodiment of the present invention.

FIG. 2 is a view showing a display example of two images. FIG. 2 shows two still images which are medial images, namely, a normal-light observation image NL and a fluorescence observation image FL, which are displayed side by side on the screen 5a of the monitor 5.

For example, when the user inputs a predetermined command for simultaneous display of two images in the keyboard 6, the control circuit 31 outputs a predetermined control signal to the synthesis circuit 38, and two moving images are simultaneously displayed on the screen 5a of the monitor 5. In the example of FIG. 2, the user displays the normal-light observation image NL by enlarging the normal-light observation image NL by the zoom function before the user presses down the freeze button 23. When the user presses down the freeze button 23, the two still images as shown in FIG. 2 are displayed on the screen 5a of the monitor 5.

Subsequently, as shown in FIG. 2, the user operates the keyboard 6, and causes a marker M to be displayed on the normal-light observation image NL, and can locate the marker M on an optional position as shown by the dotted line in FIG. 2 by using an up, a down, a left and a right arrow keys. FIG. 2 shows that the user causes the marker M to be displayed on the normal-light observation image NL, and the marker M is an arrow pointer having the shape of an arrow, and indicates a point P1 on the image of the living tissue T. Note that the user can also cause the marker M to be displayed on the fluorescence observation image FL by operating the keyboard 6.

When the user operates the zoom function to move the lens 19 to the position of the widest angle, and acquires a still image, the field of view of the normal-light observation image NL and the field of view of the fluorescence observation image FL become the same. This is because the endoscope 2 of FIG. 1 obtains the normal-light observation image and the fluorescence observation image respectively in the two CCDs 17 and 18 by using one, namely, the common lens 14 of an objective optical system and the half mirror 16 as shown in FIG. 1. When the actuator 21 outputs the termination position signal, the two observation fields of view of the CCDs 17 and 18 match each other as described above.

Figure 3:
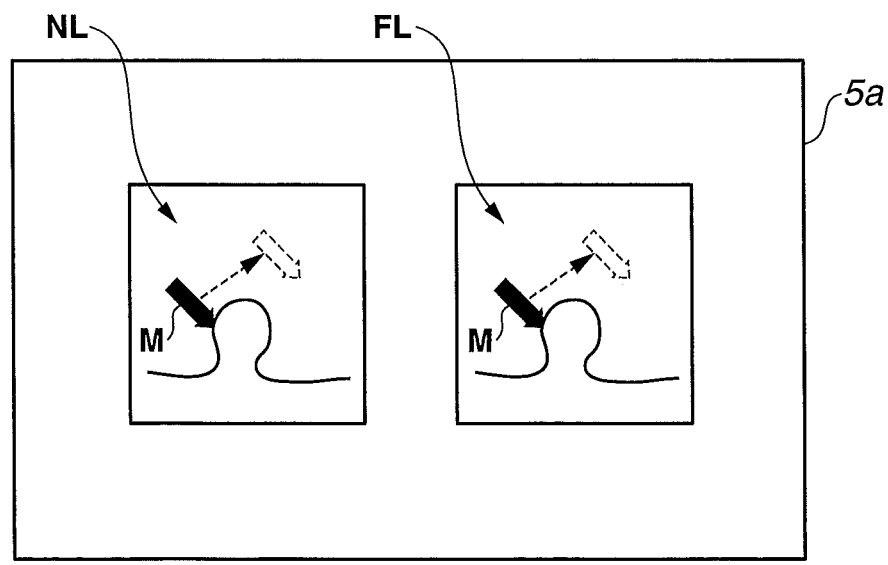
FIG. 3 is a view showing a display example of two images at a time of observation fields of view of two imagers matching each other, according to the embodiment of the present invention.

FIG. 3 is a view showing a display example of two images when the fields of view of the two imagers match each other. When the field of view of the normal-light observation image NL and the observation field of view with respect to the fluorescence observation image FL are the same, if the user operates the keyboard 6 and causes, for example, the marker M to be displayed on the normal-light observation image NL, the same marker M is also displayed on the fluorescence observation image FL. Note that in FIG. 3, the two markers M are totally the same in the shape and the color, but may be the markers having the colors and the shapes slightly changed from each other.

When the user presses down the freeze button 23 in the state in which the user moves the lens 19 to the position of the widest angle in the zoom function, the respective still images acquired in the CCDs 17 and 18 are the images of the same observation field of view.

That is to say, if the actuator 21 outputs a termination position signal when the freeze button 23 is pressed down, the two observation fields of view of the CCDs 17 and 18 match each other, and therefore, when the marker M is displayed on one of the two still images, the same marker M is displayed at the same position on the other image as shown in FIG. 3. Subsequently, when the user moves the position of the marker M on one of the two still images, the marker M on the other image similarly moves as shown by the dotted lines in FIG. 3.

Consequently, for example, when a surgeon causes the marker M to be displayed on one of the images, if the same marker M is displayed on the other image, the surgeon finds out that the positions indicated by the markers M on the two images are the same position.

As described above, the endoscope 2 is detachably connected to the processor 3 and the light source apparatus 4, and therefore, the other kinds of endoscopes can be connected to the processor 3 and the light source apparatus 4.

Figure 4:
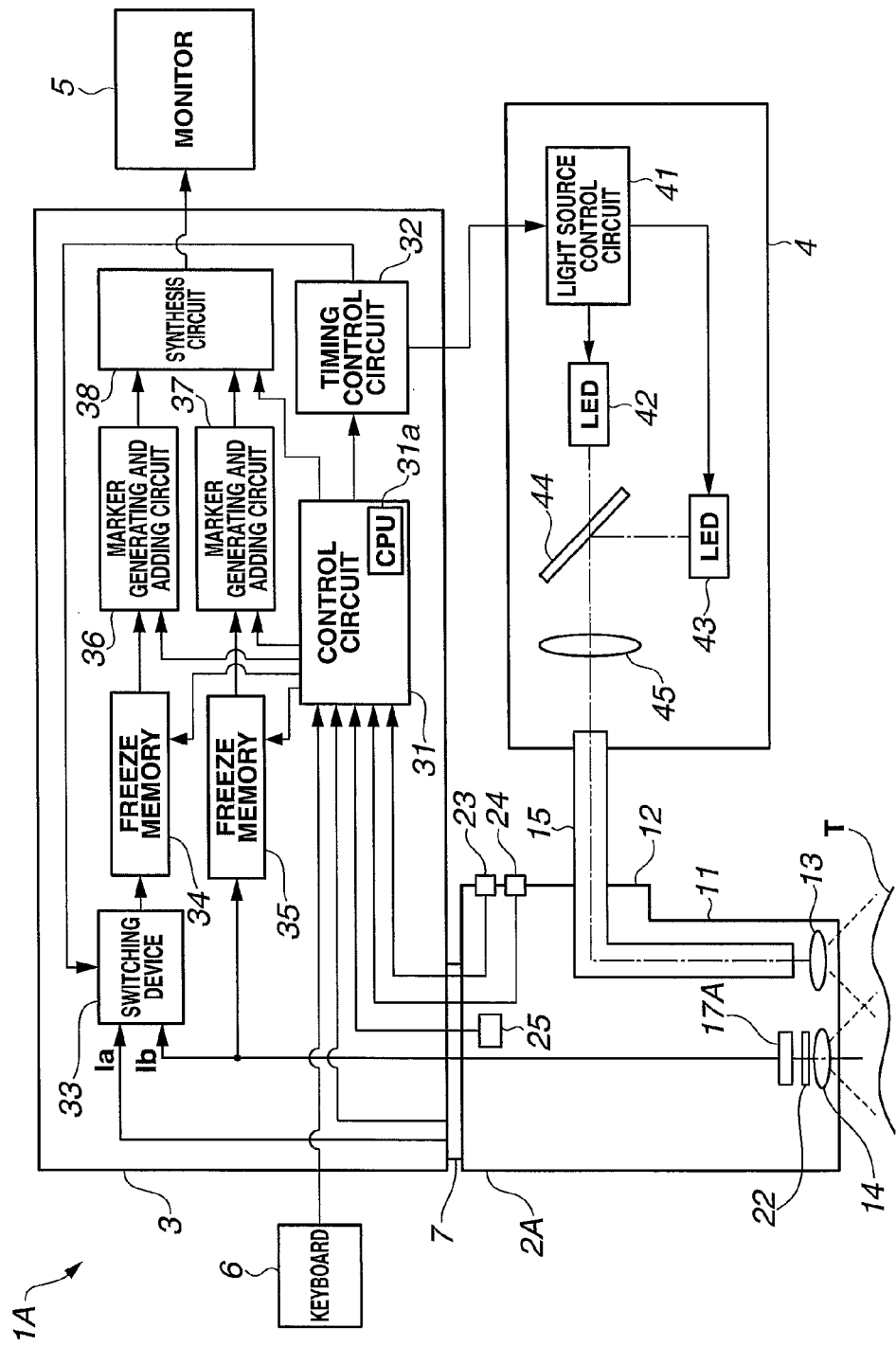
FIG. 4 is a schematic configuration diagram showing a configuration of an endoscope apparatus 1A in which an endoscope 2A different from an endoscope 2 is connected to a processor 3 and a light source apparatus 4, according to the embodiment of the present invention.

FIG. 4 is a schematic configuration diagram showing a configuration of an endoscope apparatus 1A in which an endoscope 2A different from the endoscope 2 is connected to the processor 3 and the light source apparatus 4. In FIG. 4, the same components as in FIG. 1 are assigned with the same reference signs and the description thereof will be omitted. In particular, the configurations of the processor 3 and the light source apparatus 4 are the same in FIG. 1 and FIG. 4.

The endoscope 2 shown in FIG. 1 is the endoscope in which the observation field of view with respect to the normal-light observation image NL and the observation field of view with respect to the fluorescence observation image FL sometimes match each other depending on the zoom position because the zoom function is included, whereas the endoscope 2A of FIG. 4 is the endoscope in which the observation field of view of the normal-light observation image NL and the observation field of view of the fluorescence observation image FL always match each other.

As shown in FIG. 4, in the endoscope apparatus 1A, the endoscope 2A connected to the processor 3 has one lens 14 of an objective optical system and one CCD 17A. The processor 3 controls the respective circuits to acquire the normal-light observation image NL and the fluorescence observation image FL by the CCD 17A.

The control circuit 31 reads the identification information of the identification information storage 25 of the connected endoscope 2A, and can determine a kind of the connected endoscope 2A. Accordingly, the control circuit 31 supplies a control signal corresponding to the kind of the endoscope which is determined to the timing control circuit 32, and the timing control circuit 32 supplies a timing signal corresponding to the endoscope 2A to the switching device 33. In the light source apparatus 4, the white color light for normal-light observation and the excitation light for the fluorescence observation are alternately outputted, and therefore, in synchronism with the timing, the switching device 33 selects the video signal Ib of fluorescence that is a return light corresponding to the excitation light. That is to say, the switching device 33 intermittently selects and outputs the video signal Ib which is one of the two input signals based on the timing signal from the timing control circuit 32. As shown in FIG. 4, when the endoscope 2A is connected, the timing control circuit 32 outputs a timing signal to the switching device 33 so that the switching device 33 selects the video signal Ib and outputs the video signal Ib to the freeze memory 34 at the same timing as the timing signal which is outputted to the light source apparatus 4 and drives the LED 43.

Accordingly, when the freeze button 23 is pressed down, a fluorescence observation image is stored in the freeze memory 34, and a normal-light observation image is stored in the freeze memory 35.

Figure 5:
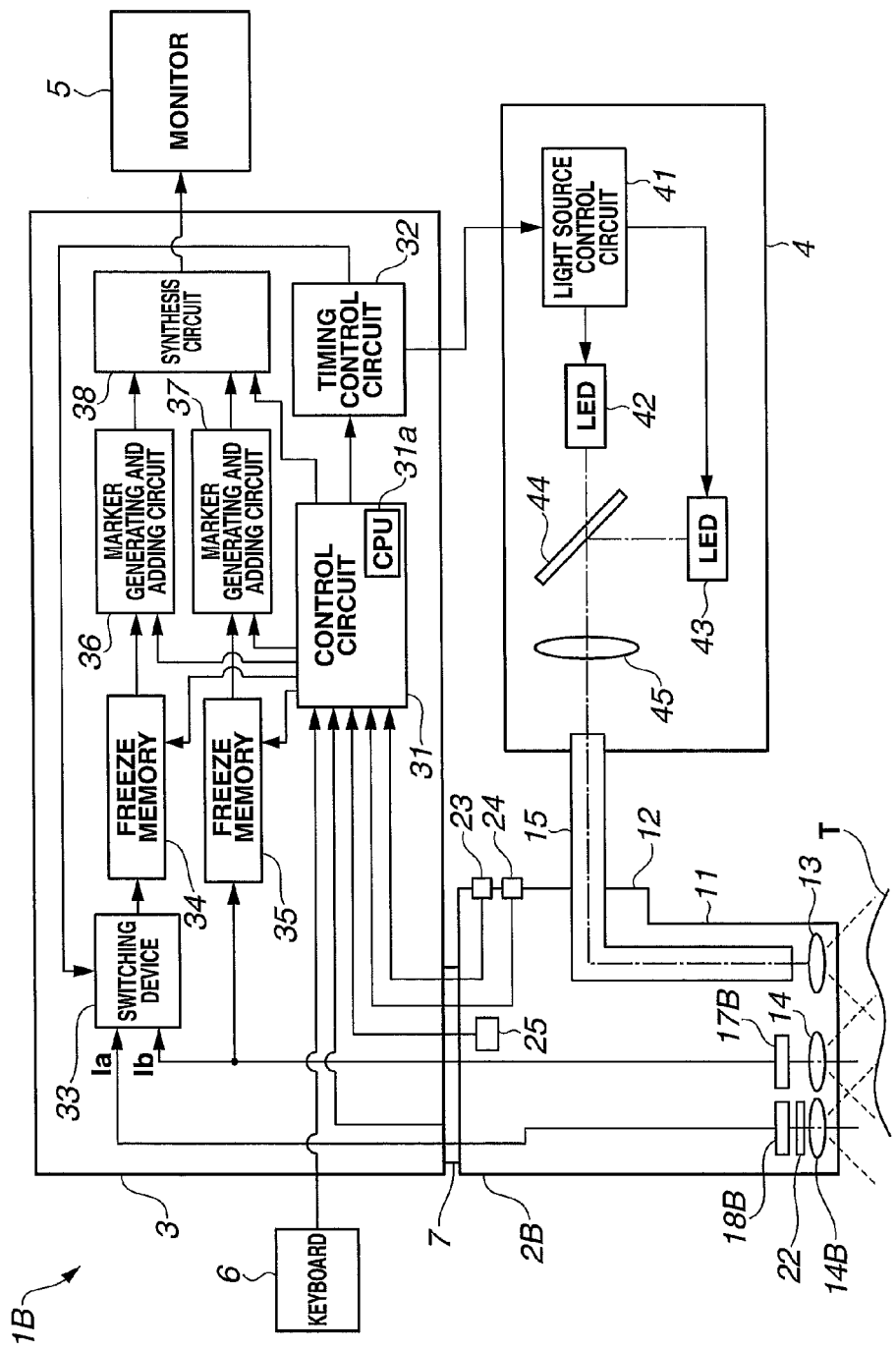
FIG. 5 is a schematic configuration diagram showing a configuration of an endoscope apparatus 1B in which an endoscope 2B different from the endoscope 2 is connected to the processor 3 and the light source apparatus 4, according to the embodiment of the present invention.

FIG. 5 is a schematic configuration diagram showing a configuration of an endoscope apparatus 1B in which an endoscope 2B different from the endoscope 2 is connected to the processor 3 and the light source apparatus 4. In FIG. 5, the same components as in FIG. 1 are assigned with the same reference signs and the description thereof will be omitted. In particular, the configurations of the processor 3 and the light source apparatus 4 are the same in FIG. 1 and FIG. 5.

The endoscope 2 shown in FIG. 1 is the endoscope in which the observation field of view with respect to the normal-light observation image NL and the observation field of view with respect to the fluorescence observation image FL sometimes match each other depending on the zoom position, and the endoscope 2A of FIG. 4 is the endoscope in which the observation field of view with respect to the normal-light observation image NL and the observation field of view with respect to the fluorescence observation image FL always match each other, whereas the endoscope 2B of FIG. 5 is an endoscope in which the observation field of view with respect to the normal-light observation image NL and the observation field of view with respect to the fluorescence observation image FL do not match each other at any time.

In the endoscope apparatus 1B, the endoscope 2B connected to the processor 3 has two CCDs 17B and 18B which pick up images via objective optical systems different from each other. The normal-light observation image NL is acquired by the CCD 17B, whereas the fluorescence observation image FL is acquired by the CCD 18B. Accordingly, in the endoscope 2B, the observation field of view with respect to the normal-light observation image NL and the observation field of view with respect to the fluorescence observation image FL do not match each other at any time.

As described above, the control circuit 31 reads the identification information of the identification information storage 25 of the connected endoscope 2B, and can determine a kind of the connected endoscope 2B. Accordingly, the control circuit 31 supplies a control signal corresponding to the kind of the determined endoscope to the timing control circuit 32, and the timing control circuit 32 supplies a timing signal corresponding to the endoscope 2B to the switching device 33. In the light source apparatus 4, the white color light for normal-light observation and the excitation light for the fluorescence observation are alternately outputted, and therefore, in synchronism with the timing, the switching device 33 selects the video signal Ia of fluorescence that is a return light corresponding to the excitation light. That is to say, the switching device 33 intermittently selects and outputs the video signal Ia which is one of the two input signals, based on the timing signal from the timing control circuit 32. As shown in FIG. 5, when the endoscope 2B is connected, the timing control circuit 32 outputs a timing signal to the switching device 33 so that the switching device 33 selects the video signal Ia and outputs the video signal Ia to the freeze memory 34 at the same timing as the timing signal which is outputted to the light source apparatus 4 and drives the LED 43.

Accordingly, when the freeze button 23 is pressed down, a fluorescence observation image which is obtained by being picked up by the CCD 18B is stored in the freeze memory 34, and a normal-light observation image is stored in the freeze memory 35.

In each of the cases of FIG. 4 and FIG. 5, the control circuit 31 reads the identification information of the identification information storage 25 of the connected endoscope, and determines matching or mismatch of the observation fields of view with respect to the two images obtained by the CCDs 17 and 18 based on the identification information. Accordingly, the control circuit 31 configures an observation field of view discriminator which determines matching of the observation fields of view with respect to the two images based on the identification information of the identification information storage 25.

(Operation)

Figure 6:
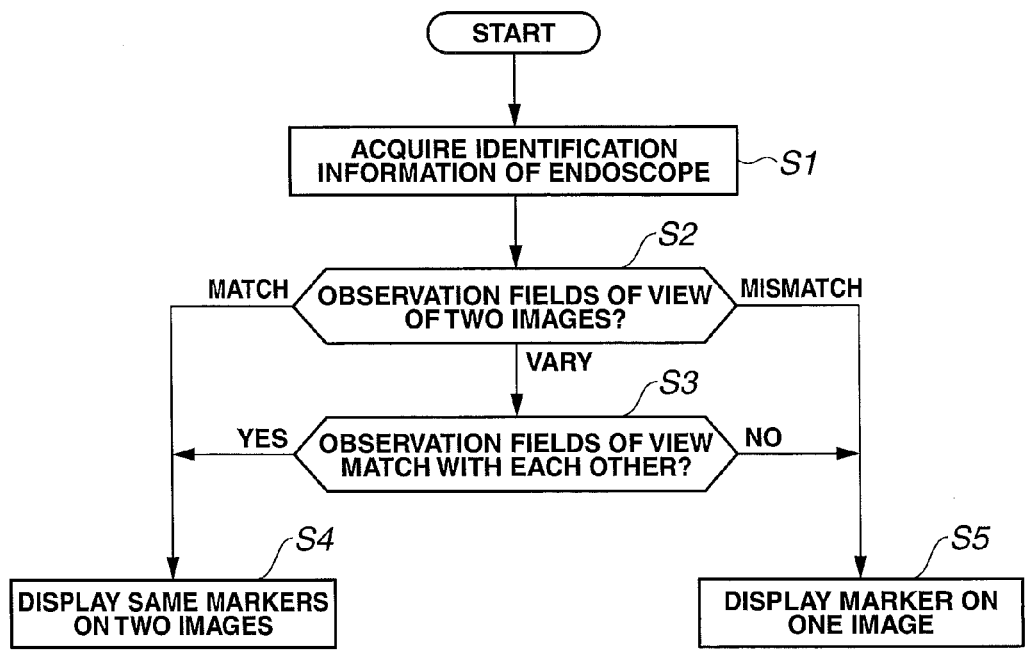
FIG. 6 is a flowchart showing an example of processing of a CPU 31a of a control circuit 31, according to the embodiment of the present invention.

FIG. 6 is a flowchart showing an example of processing of the CPU 31a of the control circuit 31. When the user issues a display instruction of the marker during operation of the processor 3, the processing of FIG. 6 is executed. Note that the processing of FIG. 6 is performed by the CPU 31a reading and executing a software program stored in a storage apparatus such as a ROM not illustrated.

The CPU 31a of the control circuit 31 reads and acquires the identification information of the identification information storage 25 of the endoscope connected to the processor 3 (S1).

The CPU 31a determines whether the observation fields of view with respect to the two images which are obtained in the endoscope always match each other, always mismatch each other, or sometimes match each other and varies, based on the read identification information (S2).

As described above, the identification information of the endoscope is the information indicating the kind of the endoscope, and from the identification information, it can be determined whether the endoscope outputs the two images with the observation fields of view always matching each other, outputs the two images with the observation fields of view always mismatching each other, or outputs the two images with the observation fields of view sometimes matching each other.

Subsequently, when the CPU 31a determines that the connected endoscope is the endoscope which outputs the two images with the observation fields of view sometimes matching each other, that is, the endoscope in which at least one of the observation fields of view of the two images varies, based on the read identification information of the endoscope, the processing proceeds to S3. In this case, the connected endoscope is the endoscope 2 as shown in FIG. 1.

In S3, the CPU 31a determines whether or not the observation fields of view match each other. The determination is performed in accordance with presence or absence of the termination position signal from the actuator 21. When the freeze button 23 is pressed down, the CPU 31a retains, namely, stores the termination position signal from the actuator 21, and therefore, the CPU 31a can perform determination of S3.

When the observation fields of view of the two images match each other (S3: YES), the CPU 31a displays the same markers M on both of the two images (S4). As shown in FIG. 3, the user can move the positions of the displayed markers M on the two images by using the up, the down, the right and the left keys or the like of the keyboard 6.

When the observation fields of view of the two images do not match each other (S3: NO), the CPU 31a displays the marker M on one of the two images (S4). As shown in FIG. 2, the user can move the position of the displayed marker on the image on which the marker M is displayed by using the up, the down, the left and the right keys or the like of the keyboard 6. Note that in FIG. 2, the marker M is displayed on the normal-light observation image NL, but the marker M can be also displayed on the fluorescence observation image FL by instruction of the user.

Further, when the CPU 31a determines that the connected endoscope is the endoscope which outputs the two images with the observation fields of view always matching each other, based on the identification information of the endoscope which is read (S2: match), the processing proceeds to S4. In this case, the connected endoscope is the endoscope 2A as shown in FIG. 4, and the observation fields of view of the two images always match each other, and therefore, the CPU 31a displays the same markers M on both of the two images (S4).

Furthermore, when the CPU 31a determines that the connected endoscope is the endoscope which outputs two images with the observation fields of view always mismatching each other, based on the identification information of the endoscope which is read (S2: mismatch), the processing proceeds to S5. In this case, the connected endoscope is the endoscope 2B as shown in FIG. 5, and the observation fields of view of the two images do not match each other at all times, and therefore, the CPU 31a displays the marker M on one of the two images (S5).

When the instruction of release of the freeze display or hiding the marker is issued, the processing of FIG. 6 ends.

As describe above, when the observation field of view discriminator determines that the observation fields of view with respect to the two images match each other, the synthesis circuit 38 displays the same markers M by superimposing the markers M on each of the two images, and when the observation field of view discriminator determines that the observation fields of view with respect to the two images do not match each other, the synthesis circuit 38 displays the markers by superimposing the marker on one of the two images.

Accordingly, when the observation fields of view of the two images match each other, the same markers M are displayed on the two images, and therefore, the user such as a surgeon can realize that the two markers M which are displayed on the two images indicate the same positions on the two images. When the marker M is displayed only on one of the two images, the user can find out that the observation fields of view with respect to the two images do not match each other.

In the above example, the same markers M are displayed on the two images when the observation fields of view with respect to the two images match each other, whereas when the observation fields of view with respect to the two images do not match each other, the marker M is displayed only on one of the images, and the marker M is not displayed on the other image. However, when the observation fields of view of the two images do not match each other, two markers in different shapes or colors from each other may be displayed on the two images.

Figure 7:
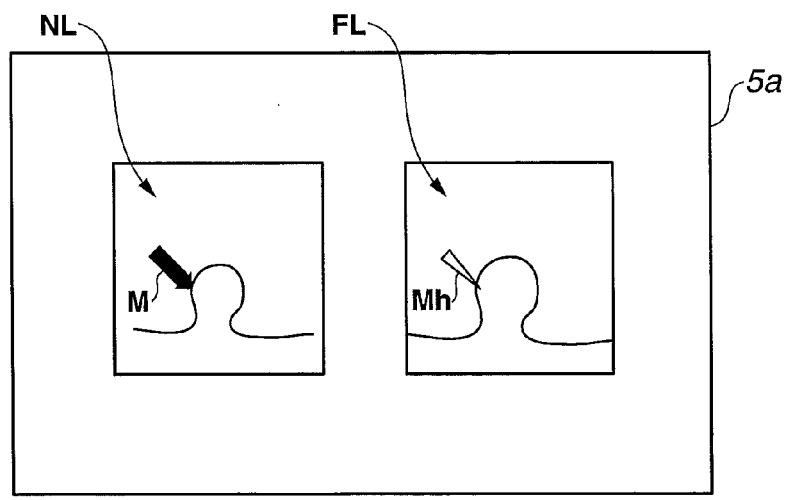
FIG. 7 is a view showing a display example of two images on a screen 5a of a monitor 5 in a case in which two markers differing from each other in at least a shape or a color are displayed on the two images, according to the embodiment of the present invention.

FIG. 7 is a view showing a display example of two images on the screen 5a of the monitor 5 in the case in which two markers differing from each other in at least one of the shape and the color are displayed on two images.

The user operates the keyboard 6, and makes setting of displaying two markers or displaying only one marker in advance when the observation fields of view with respect to the two images do not match each other. When displaying the two markers when the observation fields of view do not match each other is selected or set, and if the observation fields of view with respect to the two images do not match each other, a marker Mh differing from the marker M in the color and the shape is displayed on the fluorescence observation image FL when the user displays the marker M on the normal-light observation image NL, as shown in FIG. 7. When the observation fields of view with respect to the two images match each other, the images as shown in FIG. 3 are displayed.

Note that in FIG. 7, the marker Mh differs from the marker M in the shape and the color, but the marker Mh may be made to differ from the marker M in at least one of the shape and the color.

Figure 8:
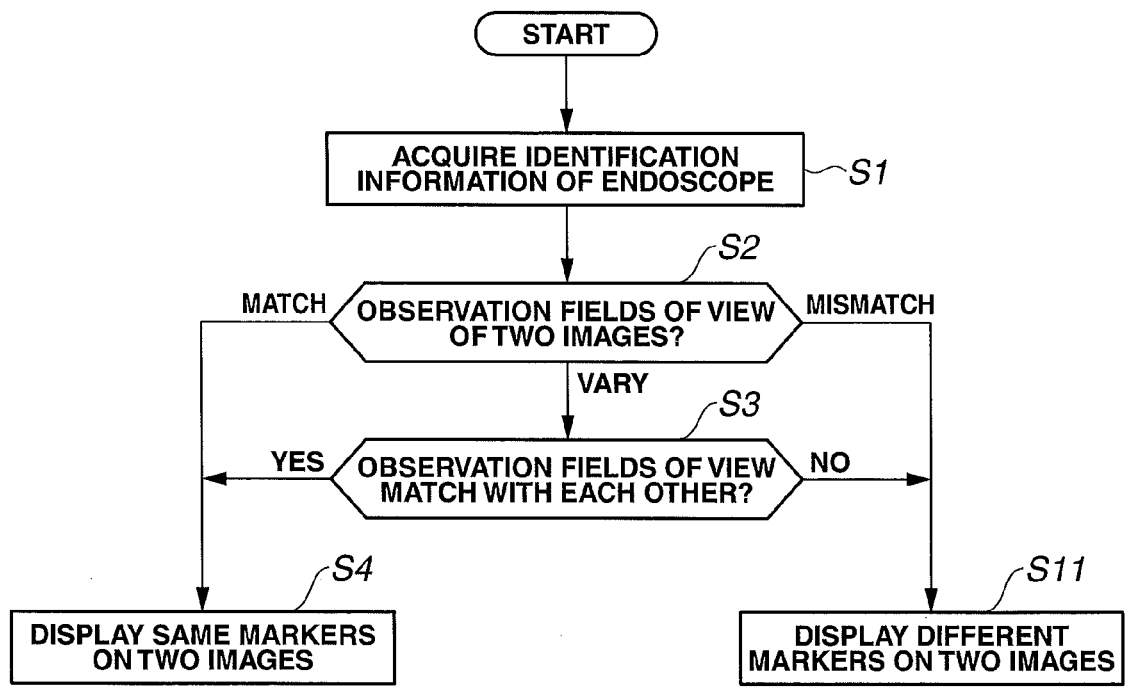
FIG. 8 is a flowchart showing an example of processing of the CPU 31a of the control circuit 31 for making the image display of FIG. 7.

FIG. 8 is a flowchart showing an example of the processing of the CPU 31a of the control circuit 31 for performing the image display of FIG. 7. In FIG. 8, the same reference signs as in FIG. 6 show the same processing and the description thereof will be omitted.

When the result is mismatch in S2, and the result is NO in S3, in FIG. 8, the processing proceeds to S11. In S11, the CPU 31a supplies the control signal of the instruction to generate and add the marker Mh which is different from the other marker to one of the marker generating and adding circuits 37 and 38, and thereby, displays the markers different from each other on the two images as shown in FIG. 7.

As above, when the observation field of view discriminator determines that the observation fields of view with respect to the two images match each other, the synthesis circuit 38 displays the same markers by superimposing the same markers on each of the two images, and when the observation field of view discriminator determines that the observation fields of view with respect to the two images do not match each other, the synthesis circuit 38 displays the markers different from each other by superimposing the markers different from each other on the two images.

Accordingly, the user can recognize whether or not the two markers indicate the same positions on the two images in accordance with the shapes or the colors of the markers which are displayed on the two images.

As above, according to the present embodiment, the medical apparatus, the method for controlling marker display in a medical images and the medical processor are provided, which can display the two markers displayed on the two images indicating the same positions on the two images. In particular, if a surgeon can find out that the observation fields of view match each other when the surgeon watches lesion ranges on the two images and compares the lesion images, the surgeon can correctly recognize the lesion range, and therefore, can perform inspection of a living tissue, treatment and the like more easily.

In FIG. 1, in the endoscope 2, one of the two imagers is provided with the zoom function, and when both of the two imagers are provided with the zoom functions, the control circuit 31 may detect the zoom amounts of the two zooms based on the outputs of the two sensors that detect the outputs of the two actuators, and may determine matching of the field of view ranges with respect to the two images.

Furthermore, the above example is the example which displays the markers on the two still images which are obtained by freezing by using the two freeze memories, but the same markers may be displayed on two moving images when the observation fields of view on the two moving images match each other, by using the frame memory for a moving picture.

The present invention is not limited to the embodiment described above, and various modifications, alterations and the like can be made within the range without departing from the gist of the present invention.

What is claimed is:

1. A medical apparatus, comprising:
    an illuminator that is capable of emitting a light for normal-light observation and a light for special-light observation to a living tissue for irradiation;

an imager that picks up an image of a light from the living tissue irradiated with the light emitted from the illuminator;

an image processor that generates a normal-light observation image obtained by picking up an image of a light from the living tissue irradiated with the light for normal-light observation in a first observation field of view in the imager, and further a special-light observation image obtained by picking up an image of a light from the living tissue irradiated with the light for special-light observation in a second observation field of view in the imager;

a discriminator that determines matching of the first observation field of view and the second observation field of view;

a processor that performs processing for displaying markers indicating the same position for the normal-light observation image and the special-light observation image when it is determined that the first observation field of view and the second observation field of view match each other in the discriminator, the processor performing processing for displaying the marker to be superimposed on each of the normal light observation image and the special-light observation image when it is determined that the first observation field of view and the second observation field of view match each other by the discriminator, and displaying the marker to be superimposed on one of the normal-light observation image and the special-light observation image when it is determined that the first observation field of view and the second observation field of view do not match each other by the discriminator; and a display that simultaneously displays the normal-light observation image and the special-light observation image processed in the processor.

2. The medical apparatus according to claim 1, wherein the processor performs processing for displaying the marker to be superimposed on each of the normal-light observation image and the special-light observation image when it is determined that the first observation field of view and the second observation field of view match each other by the discriminator, and performs processing for displaying markers different from each other to be superimposed on the normal-light observation image and the special-light observation image, when it is determined that the first observation field of view and the second observation field of view do not match each other by the discriminator.

3. The medical apparatus according to claim 1, wherein the discriminator determines matching of the first observation field of view and the second observation field of view based on identification information of an endoscope having the imager.

4. The medical apparatus according to claim 1,
wherein the imager has a zoom lens that makes an observation field of view range variable, and
the discriminator determines matching of the first observation field of view and the second observation field of view based on zoom information of the zoom lens.

5. The medical apparatus according to claim 4, wherein the zoom information is information at a time of the normal-light observation image or the special-light observation image being picked up.

6. The medical apparatus according to claim 1,
wherein the imager has a zoom lens that makes an observation field of view range variable, and
the discriminator determines matching of the first observation field of view and the second observation field of view based on identification information of an endoscope having the imager and zoom information of the zoom lens.

7. The medical apparatus according to claim 6, wherein the zoom information is information at a time of the normal-light observation image or the special-light observation image being picked up.

8. The medical apparatus according to claim 1, wherein the imager has a first imager that picks up an image of a return light of the light for normal-light observation and a second imager that picks up an image of a return light of the light for special-light observation.

* * * * *